United States Patent [19]

Alexander et al.

[11] Patent Number: 6,143,281
[45] Date of Patent: Nov. 7, 2000

[54] DENTIFRICE COMPOSITIONS

[75] Inventors: Stephan Edward Alexander; Geoffrey Royston Doel; Peter John Edwards, all of Weybridge, United Kingdom

[73] Assignee: SmithKline Beecham p.l.c., Brentford, United Kingdom

[21] Appl. No.: 09/322,763

[22] Filed: May 26, 1999

Related U.S. Application Data

[63] Continuation of application No. 08/307,023, Sep. 14, 1994, which is a continuation of application No. 07/032,445, Mar. 31, 1987, abandoned, which is a continuation of application No. 07/420,153, Oct. 11, 1989, abandoned.

[30] Foreign Application Priority Data

| Oct. 13, 1988 | [GB] | United Kingdom | 8824073 |
| Nov. 30, 1988 | [GB] | United Kingdom | 8827913 |
| Aug. 1, 1989 | [GB] | United Kingdom | 8917580 |

[51] Int. Cl.$^7$ .............................. A61K 7/16; A61K 7/18; A61K 7/22
[52] U.S. Cl. .................................. 424/54; 424/49; 424/52
[58] Field of Search .......................................... 424/49–58

[56] References Cited

U.S. PATENT DOCUMENTS

| 2,684,924 | 7/1954 | Rose et al. . |
| 2,863,919 | 12/1958 | Birtwell . |
| 2,990,425 | 6/1961 | Senior . |
| 3,804,946 | 4/1974 | Harrison et al. . |
| 3,842,168 | 10/1974 | Colodney . |
| 3,843,779 | 10/1974 | Norfleet . |
| 3,937,805 | 2/1976 | Harrison . |
| 3,966,863 | 6/1976 | Forward et al. . |
| 3,976,765 | 8/1976 | Nachtigal . |
| 3,989,813 | 11/1976 | Januszewski et al. . |
| 4,025,616 | 5/1977 | Haefele . |
| 4,241,049 | 12/1980 | Colodney et al. . |
| 4,248,860 | 2/1981 | Watson . |
| 4,273,759 | 6/1981 | Gaffar et al. . |
| 4,323,552 | 4/1982 | Schmolka . |
| 4,332,791 | 6/1982 | Raaf et al. . |
| 4,339,429 | 7/1982 | Raaf et al. . |
| 4,340,583 | 7/1982 | Wason . |
| 4,358,437 | 11/1982 | Duke . |
| 4,495,167 | 1/1985 | Mauroth et al. . |
| 4,565,691 | 1/1986 | Jackson . |
| 4,631,184 | 12/1986 | Winyall et al. . |
| 4,656,031 | 4/1987 | Lane et al. . |
| 4,661,342 | 4/1987 | Yamazaki et al. . |
| 4,753,791 | 6/1988 | Muller et al. . |
| 4,828,824 | 5/1989 | Grollier . |
| 4,973,462 | 11/1990 | Akiri et al. . |
| 4,992,251 | 2/1991 | Aldcroft et al. . |
| 5,034,207 | 7/1991 | Kerner et al. . |
| 5,035,879 | 7/1991 | Aldcroft et al. . |
| 5,110,574 | 5/1992 | Reinharot . |
| 5,234,673 | 8/1993 | McGill et al. . |
| 5,286,478 | 2/1994 | Persello . |
| 5,419,888 | 5/1995 | McGill et al. . |

FOREIGN PATENT DOCUMENTS

| 0026252 | 4/1981 | European Pat. Off. . |
| 0315503 | 5/1989 | European Pat. Off. . |
| 0368130 | 5/1990 | European Pat. Off. . |
| 2341302 | 9/1977 | France . |
| 3415147 | 10/1985 | Germany . |
| 50-76243 | 1/1975 | Japan . |
| 51-51530 | 1/1976 | Japan . |
| 54-11243 | 1/1979 | Japan . |
| 59-101417 | 1/1984 | Japan . |
| 59-101418 | 1/1984 | Japan . |
| 60-130511 | 1/1985 | Japan . |
| 1249742 | 10/1971 | United Kingdom . |
| 1302019 | 1/1973 | United Kingdom . |
| 1436487 | 5/1976 | United Kingdom . |
| 1506045 | 4/1978 | United Kingdom . |
| 2035084 | 6/1980 | United Kingdom . |
| 2037162 | 7/1980 | United Kingdom . |
| 159 26 60 | 7/1981 | United Kingdom . |
| WOI9005113 | 5/1990 | WIPO . |

*Primary Examiner*—Shep K. Rose
*Attorney, Agent, or Firm*—Nora Stein-Fernandez; Janice E. Williams; Charles M. Kinzig

[57] ABSTRACT

The problem of formulating a dentifrice which is compatible with a bis-biguanide anti-bacterial agent, for instance chlorhexidine or alexidine, is solved by using a nonionic thickening agent; a nonionic surfactant; and an abrasive which is either a sparingly soluble salt, for instance calcium carbonate, (used in combination with an agent to suppress anion formation), or an essentially insoluble compound, for instance, a silica of low anion content, or a mixture thereof. Preferably, the composition has a flavor which is mainly aniseed, balanced by mints. Preferably during the preparation of a silica containing dentifrice, chlorhexidine and saccharin are added together at an early stage, prior to the addition of silica, to avoid the formation of lumps. Such dentifrices are useful in the prophylaxis and/or treatment of periodontal disease and caries.

10 Claims, No Drawings

DENTIFRICE COMPOSITIONS

This is a continuation of application Ser. No. 08/307,023, filed Sep. 14, 1994 which is a continuation of application Ser. No. 07/032,445, filed Mar. 31, 1987, now abandoned, which is a continuation of application Ser. No. 07/420,153, filed Oct. 11, 1989, now abandoned.

The present invention relates to a dentifrice composition comprising an antibacterial agent, in particular an agent selected from the bis-biguanide group of antibacterials, which compositions are useful in the prophylaxis and/or treatment of periodontal disease and caries.

The bis-biguanide group of antibacterial agents have been disclosed in U.S. Pat. Nos. 2,684,924, 2,990,425, 2,830,006 and 2,863,019.

In particular, attention has focussed on two bis-biguanides viz chlorhexidine [N,N''-bis(4-chlorophenyl)-3,12-diimino-2,4,11,13-tetraazatetradecanediimidamide or 1,1'-hexamethylene-bis-[5-(p-chlorophenyl)biguanide], the compound of formula (A):

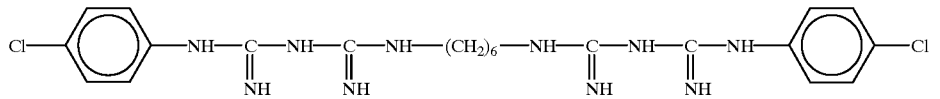

and the corresponding compound alexidene in which the chlorophenyl groups have been replaced by 2-ethylhexyl groups.

Chlorhexidine is a well established antimicrobial agent which has found use in a wide variety of applications as an antiseptic or disinfectant. In the area of oral hygiene, mouthwashes and a gel comprising chlorhexidine are commercially available. Further use of the agent has however been limited by the known propensity of chlorhexidine to form insoluble salts which remove it from solution and thereby render it unavailable. In addition, chlorhexidine has a bitter taste and tends to stain plaque brown. The latter may be minimised by using a dentifrice, rather than a mouthwash, as the abrasive incorporated therein removed plaque. The formulation of an acceptable dentifrice however provides a stern challenge, due to the multitude of components incorporated therein, each of which may be incompatible with chlorhexidine.

Various proposals have been made over the years to try and overcome the incompatibility problem, by examining various aspects of the dentifrice, for instance, the abrasive, the surfactant, the thickening agent and the process for preparation of the dentifrice.

Specific suggestions for suitable abrasives include the use of (i) abrasives coated with a cationic water soluble polymer (GB 1 506 045, to Procter+Gamble Co.), (ii) silica of a defined particle size (30% less than 5 mu) (GB 1 249 842, to Colgate-Palmolive Co.), and (iii) the use of either α-alumina monohydrate (GB 2 037 162, to Unilever NV) or α-alumina trihydrate (GB 1 302 019, to Colgate-Palmolive Co.).

Recently, EP-A-0 315 503 (to Rhone-Poulenc Chimie) (published after the earliest priority date of the present application) has disclosed the suitability of particular types of silicas, characterised by inter alia, a low anion (<1%) content. Whilst the compatibility of these silicas with chlorhexidine and with other dentifrice ingredients was established by a spectrophotometric assay, no consideration was given to the compatibility of chlorhexidine with the other ingredients.

Specific suggestions for suitable surfactants include the use of either an amphoteric surfactant (in combination with a nonionic thickening agent such as hydroxyethyl cellulose) (JP 51 051 530, to Lion Fat and Oil KK); or a polyoxyethylene fatty ester to augment an anionic surfactant (in combination with an anionic thickening agent, such as sodium carboxymethyl cellulose) (JP 50 076 243, to Sunstar Dentifrice KK). The natural gum carrageenan was suggested to be a suitable thickening agent (JP 79 011 243, Lion Dentifrice Co.).

It has also been suggested that either ethanol or a water soluble alkaline earth metal salt (when the dentifrice also includes a phosphate salt) may be added, to stabilise chlorhexidine in a dentifrice comprising otherwise conventional components (U.S. Pat. No. 3,989,813 and U.S. Pat. No. 4,241,049, both to Colgate-Palmolive Co.). Similarly, the use of a phenol or a higher alcohol has been proposed, to stabilise a dentifrice comprising chlorhexidine and a nonionic surfactant (JP 59 101 417, JP 59 101 418, both to Lion Corporation).

U.S. Pat. No. 4,273,759 (to Colgate-Palmolive Co.) discloses a chlorhexidine dentifrice comprising hydrated alumina, a nonionic surfactant and hydroxypropyl methylcellulose.

FR 2 341 302 (to Pierre Fabre SA) discloses the use of a microbiological assay for assessing the compatibility of chlorhexidine with various types of conventional dentifrice ingredient. Anionic surfactants, the abrasive bentonite and carragheen and alginate gums were found to be unsuitable.

The appropriate sequence of addition of the various components has been identified as being of importance in the maintainance of chlorhexidine in a soluble form in the formulation (U.S. Pat. No. 3,843,779 and U.S. Pat. No. 3,842,168, both to Colgate-Palmolive Co., and JP 60 130 511, to Lion Corporation).

Several methods of overcoming the unpleasant bitter flavour associated with chlorhexidine have been disclosed, including the use, in an alumina-based dentifrice, of a predominantly peppermint flavour, moderated by the addition of an aniseed flavour (GB 2 035 084, to Unilever).

In spite of all these proposals, as far as we are aware, no dentifrice comprising an effective amount of chlorhexidine or any other bis-biguanide antibacterial agent is currently available commercially.

It has now been discovered that this problem of incompatability can be overcome or at least mitigated by the use of a particular formulation of dentifrice.

Accordingly, the present invention provides a dentifrice comprising:

(a) a bacteriostatically effective amount of a bis-biguanide compound of formula (I):

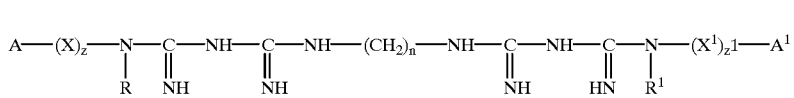

wherein
- A and $A^1$ each represent (i) a phenyl group optionally substituted by $(C_{1-4})$alkyl, $(C_{1-4})$alkoxy, nitro, or halogen, (ii) a $(C_{1-12})$alkyl group, or (iii) a $(C_{4-12})$ alicyclic group;
- X and $X^1$ each represent $(C_{1-3})$alkylene;
- R and $R^1$ each represent hydrogen, $(C_{1-12})$alkyl, or aryl$(C_{1-6})$alkyl;
- Z and $Z^1$ are each 0 or 1;
- n is an integer from 2 to 12;
- and the polymethylene chain $(CH_2)_n$ may optionally be interrupted by oxygen or sulphur or an aromatic (for instance phenyl or naphthyl) nucleus;
- or an orally acceptable acid addition salt thereof, in aqueous solution;

(b) a nonionic thickening agent;
(c) a nonionic surfactant; and
(d) an abrasive which comprises either:
  (i) at least one sparingly soluble salt, in combination with an agent to suppress anion formation; or
  (ii) at least one essentially insoluble compound,
  or a mixture thereof,
  with the proviso that the abrasive does not consist essentially of calcium pyrophosphate, trimagnesium phosphate, alumina, hydrated alumina, an aluminium silicate or a mixture thereof.

Advantageously, the bis-biguanide of formula (I) is present in the range 0.005 to 10%, preferably 0.005 to 5%, more preferably 0.005 to 2.5% by weight of the dentifrice, calculated as the free base.

Examples of bis-biguanides of formula (I) are chlorhexidine and alexidine, of which chlorhexidine is particularly preferred.

Suitable acid addition salts of the bis-biguanides of formula (I) include the diacetate, the dihydrochloride and the digluconate.

Suitable acid addition salts of chlorhexidine are those which have a water solubility at 20° C. of at least 0.005% w/v and include the digluconate, diformate, diacetate, dipropionate, dihydrochloride, dihydroiodide, dilactate, dinitrate, sulphate, and tartrate salts. Preferably the salt is the dihydrochloride, diacetate or digluconate salt.

Suitable acid addition salts of alexidine include the dihydrochloride salt.

Suitable nonionic thickening agents include $(C_{1-6})$ alkylcellulose ethers, for instance methylcellulose, and $(C_{2-6})$alkylene oxide modified $(C_{1-6})$alkylcellulose ethers, for instance hydroxypropyl methylcellulose, and mixtures thereof.

Preferably, the nonionic thickening agent is a low viscosity grade of hydroxypropyl methylcellulose which may advantageously be used in combination with a high viscosity grade of hydroxypropyl methylcellulose, the mixture being balanced to give the formulation the required viscosity.

Suitable grades of hydroxypropyl methylcellulose are marketed under the trade name 'Methocel' by Dow Chemical Corporation. The grades 'Methocel K15M' (high viscosity) and 'Methocel K100LV' are found to be particularly useful, an effective ratio thereof being in the range of from 1:50 to 1:1, preferably 1:20 to 1:2.

Advantageously, the nonionic thickening agent is present in the range 0.01 to 30%, preferably 0.1 to 15%, more preferably 1 to 5%, by weight of the dentifrice.

Suitable nonionic surfactants include, for instance polyethoxylated sorbitol monoesters (for instance, the products marketed under the trade name 'Tween' by ICI), polycondensates of ethylene oxide and propylene oxide (poloxamers) (for instance the products marketed under the trade name 'Pluronic' by BASF-Wyandotte), condensates of propylene glycol and polyethoxylated hydrogenated castor oil (for instance, cremophors).

Advantageously, the surfactant is present in the range 0.005 to 20%, preferably 0.1 to 10%, more preferably 0.1 to 5% by weight of the dentifrice.

Suitable sparingly soluble salts that may be used as an abrasive include calcium carbonate, calcium phosphates, magnesium carbonate, insoluble sodium metaphosphate, and suitable mixtures thereof. The agent to suppress anion formation typically comprises a water soluble salt containing a cation which may be same as the cation of the abrasive and which forms an essentially insoluble or sparingly soluble salt with the anion of the abrasive.

Preferably the sparingly soluble salt used as an abrasive is calcium carbonate, advantageously used in combination with dicalcium phosphate, which also usefully buffers the pH of the formulation. Suitable types of calcium carbonate include both natural and synthetic chalks.

The agent to suppress anion formation may be an alkaline earth metal salt, for instance calcium chloride. The agent is preferably present in from 0.0001 to 1%, more preferably 0.005 to 0.1% by weight of the dentifrice.

The term 'essentially insoluble compound' as used herein refers to a compound which is intrinsically insoluble in aqueous solution and includes those compounds which are listed as being 'insoluble' in cold water in the 'Handbook of Chemistry and Physics', 48th Edition, Chemical Rubber Company, Section B, Physical Constants of Inorganic Compounds. Furthermore, such compounds when used as an abrasive shall contain little if any contaminating anionic impurities. Preferably the insoluble abrasive compound contains less than 1%, more preferably less than 0.5%, of anionic impurities, based on the weight of the abrasive.

Suitable essentially insoluble compounds for use as abrasives include silica, zinc orthophosphate, plastics particles or mixtures thereof; of which silica is preferred.

The preferred silica abrasive may be a natural amorphous silica, for instance diatomaceous earth; or a synthetic amorphous silica, for instance a precipitated silica, or a silica gel, such as a silica xerogel; or mixtures thereof.

The preferred grades of synthetic amorphous silica are those for which the manufacturing process is carefully controlled so that the level of anion impurities, particularly sulphate and silicate from sodium sulphate and sodium silicate, respectively, is kept to a minimum. Alternatively, or in addition, the level of anion impurities may be reduced to the required level by careful washing of the silica with, for instance, deionised or distilled water.

Suitable silicas include those described in EP-A-0 315 503 (to Rhone-Poulenc) which are characterised as having:
(i) less than $5 \times 10^{-3}$, preferably less than $1 \times 10^{-3}$, more preferably less than $0.2 \times 10^{-3}$ moles of anions per 100 g of silica, and in particular less than 0.5%, preferably less than 0.1%, more preferably less than 0.02% by weight of silica of sulphate anions;

(ii) a Hammett acidity function Ho of at least 3.3, which may be determined according to the method of Walling, J. Amer. Chem. Soc., 1950, 72, 1164;

(iii) a surface in which the number of hydroxyl groups, expressed as $OH/nm^2$ is less than 15, more particularly less than 12, which number may be determined according to the method described in EP-A-0 315 503; and (iv) a point zero charge of at least 3 and preferably between 4 and 6, which point zero charge may be determined according to the method described in EP-A-0 315 503.

Such silicas may be prepared as precipitates or gels from silicate and acid by conventional means, the crude silica product being collected and then washed with water, preferably deionised water, until the conductivity of the washings is less than 200 microsiemens $cm^{-1}$, preferably less than 200 microsiemens $cm^{-1}$, and then dried and, if necessary, ground to give the desired sizes of particles. Alternatively, an initial washing of the crude product with water, until the washings have a conductivity of less than 2000 microsiemens $cm^{-1}$, may be followed by washing with an acid or an aqueous acid, for instance a mineral acid such as nitric acid, or an organic acid such as acetic acid or citric acid, until the silica has a pH of less than 8, preferably between 6 and 7.5.

Suitable silica xerogels are described in U.S. Pat. No. 3,538,230.

Suitable grades of precipitated silica have BET surface areas in the range 20 to 300, preferably 20–100 $m^2/g$ and median agglomerate sizes in the range 2 to 50, preferably 5 to 30μ.

Preferred precipitated silicas are those marketed under the trade name 'Sident' by Degussa. Preferred silica xerogels are those marketed under the trade name 'Syloblanc' by W. R. Grace Corporation, Davison Chemical Division.

Suitable forms of diatomaceous earth include those marketed under the trade name 'Celite' by Johns-Manville Products Corporation, for instance 'Celite Superfine Superfloss'.

Preferably the silica abrasive comprises diatomaceous earth which may advantageously be used in combination with a synthetic amorphous silica, in particular a precipitated silica (as hereinbefore defined), which also usefully buffers the pH of the formulation and counters the otherwise off-white colour and roughness conferred upon a formulation by the use of a diatomaceous earth alone. Suitably, the ratio of diatomaceous earth to synthetic amorphous silica is from 5:1 to 1:5, preferably about 1:1.

The abrasive is advantageously present in the range 1–80%, preferably 5–70%, more preferably 5–60% by weight of the dentifrice.

In another aspect of this invention it has been found that when certain of the insoluble compounds, for instance, silica, zinc orthophosphate, or plastics particles are used as the abrasive, a fluoride salt such as an alkali metal fluoride may also be incorporated into the formulation, to provide between 100 and 3000 ppm, preferably 500 to 2000 ppm of fluoride. Preferably the fluoride salt is an alkali metal fluoride, for instance sodium fluoride. Other fluorides that may be used include amine fluorides.

Dentifrices according to the invention may also contain a humectant, such as glycerine, sorbitol, propylene glycol or polyethylene glycol, or mixtures thereof; which humectant may be present in the range 5 to 30%, preferably 10 to 30% by weight of the dentifrice. Preferably the humectant is glycerine.

Dentifrices according to the invention may also contain other agents conventionally used in dentifrice formulations, for instance flavouring agents; colouring agents; whitening agents; preservatives and sweetening agents. It will be appreciated that such agents (at the level employed) should be compatible with the bis-biguanide of formula (I); that is, the agent will not substantially reduce the availability of the bis-biguanide of formula (I). This may be confirmed by, for instance, determining the biological activity of the formulation, (by following the method provided in the 'Biological Data' section) in the presence and absence of the agent. In general, such agents will be a minor amount or proportion of the formulation, usually present in from 0.001 to 5% by weight of the composition.

Flavour is an important aspect of the consumer acceptability of a dentifrice. This is particularly so in the case of a dentifrice comprising a bis-biguanide of formula I, especially chlorhexidine, because of the bitter after-taste of the bis-biguanide. Surprisingly it has now been found that this can be effectively masked by an aniseed flavour.

Accordingly, in a further aspect, the present invention provides a dentifrice as hereinbefore defined which further comprises a flavouring agent having an aniseed flavour.

Flavouring agents having an aniseed flavour including anethole, which may be present in such quantity as to mask the bitter after-taste of the bis-biguanide of formula (I).

Preferably the flavour may be modified by the additional incorporation of one or more flavouring agents having a mint flavour, to balance the aniseed flavour, to give a flavour which has more general consumer acceptability but in which the aniseed flavour is still dominant.

Suitable flavouring agents having a mint flavour include peppermint, spearmint, menthol and carvone.

Preferably more than one mint flavouring agent is used, of which menthol may be the major component, accounting for between 20 and 60%, preferably between 25 and 55% by weight of the flavouring agents having a mint flavour.

Advantageously the flavour of the dentifrice may be further modified by the incorporation of flavouring agents having spicey flavours such as coriander, eugenol and eucalyptol, the aniseed flavour still being dominant.

Accordingly, in a still further aspect, the invention provides a dentifrice as hereinbefore defined comprising aniseed and mint flavours and, optionally, spicey flavours, and having a predominantly aniseed flavour.

Preferably, in such a dentifrice comprising aniseed and mint flavours, flavouring agents having an aniseed flavour comprise from 10 and 30%, more preferably 15 to 25% of the combined weights of the flavouring agents, whilst flavouring agents having a mint flavour comprise from 40 to 80, preferably 40 to 70% of the combined weight of the flavouring agents. Preferably the combined flavouring agents comprise up to 5%, more preferably up to 2% by weight of the dentifrice.

Suitable sweetening agents include saccharin and acceptable water soluble salts thereof, such as the sodium salt, and may be present in from 0.01 to 0.5%, preferably 0.05 to 0.5% by weight of the dentifrice. An auxiliary sweetener such as a thaumatin may also be included, at a level of from 0.001 to 0.1, preferably 0.005 to 0.05% by weight of the dentifrice. A suitable blend of thaumatins is marketed under the trade name 'Talin' by Tate and Lyle plc.

Accordingly, in a preferred aspect, the invention provides a dentifrice as hereinbefore defined, comprising aniseed and mint flavours, in combination with saccharin, or the sodium salt thereof, and a thaumatin.

Water, preferably deionised or distilled water, will also be present, in the range from 10 to 80%, preferably 20 to 70% by weight of the dentifrice.

The dentifrices according to the invention may have a pH within the range pH 4 to 10, preferably pH 5 to 8.

In an especially preferred aspect, the invention provides a dentifrice comprising:

(i) chlorhexidine or an acid addition salt thereof;

(ii) a ($C_{2-6}$)alkylene oxide modified ($C_{1-6}$)alkyl cellulose thickening agent;

(iii) a poloxamer surfactant; and (iv) an abrasive which is either:
   (a) a precipitated silica in which the anion content is less than 1%, optionally in combination with diatomaceous earth, or
   (b) calcium carbonate, optionally in combination with dicalcium orthophosphate and comprising an alkaline earth salt to act as an anion suppressant agent.

The dentifrices according to the invention are prepared in a conventional manner by mixing the ingredients thereof in the required proportions and in any order which is convenient and, thereafter and if necessary, adjusting the pH. For instance, the nonionic thickening agent and the humectant and part of the water are vigourously agitated together, with heat, if necessary, to give a hydrated gel. Abrasive is then dispersed in this hydrated gel, using a heavy-duty mixing machine, with active agents, such as chlorhexidine, or a salt thereof, a fluoride salt (if present), then added, followed by nonionic surfactant and flavouring agents in the final stage; with final mixing carried out under vacuum.

It has been found that in the particular instance of a dentifrice according to the invention comprising chlorhexidine (or an acid addition salt thereof), a silica abrasive and sodium saccharin, a smoother formulation, which has improved storage stability, with respect to the formation of lumps (which are believed to be a silica-containing form of chlorhexidine saccarinate), may be obtained if chlorhexidine, or a salt thereof, is added at an earlier, rather than a later, stage of the manufacturing process.

Accordingly, in a further aspect, the invention provides a process for the preparation of a dentifrice comprising chlorhexidine, or an acid addition salt thereof, a silica abrasive, and saccharin, or a salt thereof, which process comprises the steps of:

(i) at an earlier stage of the process, substantially simultaneously adding chlorhexidine, or an acid addition salt thereof, and saccharin, or a salt thereof, and (ii) at a later stage of the process, adding silica; and optionally, as a preliminary step to the aforementioned steps, forming a hydrated gel by the admixing of water, humectant and nonionic thickening agent.

The invention also provides a method for the prophylaxis or treatment of periodontal disease and/or caries, which method comprises the application of a dentifrice according to the invention to the oral cavity.

The following examples illustrate the invention.

EXAMPLE 1

Chalk Based Toothpaste

| | |
|---|---|
| Chlorhexidine digluconate | 1.00% |
| Glycerin | 18.00 |
| Hydroxypropyl methylcellulose | 3.60 |
| Chalk | 32.00 |
| Dicalcium phosphate dihydrate | 3.00 |
| Calcium chloride solution (1%) | 1.00 |
| Flavour | 1.00 |
| Poloxamer 338 | 2.00 |
| Deionized water | q.s. |

EXAMPLE 2

Silica Based Toothpaste

| | |
|---|---|
| Chlorhexidine digluconate | 1.00% |
| Glycerin | 18.00 |
| Hydroxypropyl methylcellulose | 3.60 |
| Silica[1] | 16.00 |
| Sodium fluoride | 0.23 |
| Flavour | 1.00 |
| Poloxamer 338 | 2.00 |
| Deionized water | q.s. |

[1]The silica was prepared by washing Syloblanc 31 (available from W.R. Grace Corporation) with deionised water (twice), followed by drying at 50° C.

EXAMPLE 3

Diatomaceous Earth Based Toothpaste

| | |
|---|---|
| Chlorhexidine digluconate | 1.00% |
| Glycerin | 18.00 |
| Hydroxypropyl methylcellulose | 3.60 |
| Diatomaceous earth | 16.00 |
| Sodium fluoride | 0.23 |
| Flavour | 1.00 |
| Poloxamer 338 | 2.00 |
| Deionized water | q.s. |

EXAMPLE 4

Zinc Orthphosphate Based Toothpaste

| | |
|---|---|
| Chlorhexidine digluconate | 1.00% |
| Glycerin | 24.00 |
| Hydroxypropyl methylcellulose | 5.00 |
| Zinc orthophosphate | 16.00 |
| Sodium fluoride | 0.23 |
| Flavour | 1.00 |
| Poloxamer 338 | 2.00 |
| Deionized water | q.s. |

EXAMPLE 5

Diatomaceous Earth/Silica Based Toothpaste

| | |
|---|---|
| Chlorhexidine digluconate | 1.00% |
| Glycerin | 18.00 |
| Hydroxypropyl methylcellulose[1] | 3.60 |
| Diatomaceous earth | 8.00 |
| Silica[2] | 8.00 |
| Sodium fluoride | 0.23 |
| Flavour[3] | 1.00 |
| Sodium saccharinate | 0.10 |
| Thaumatin | 0.02 |

-continued

| Diatomaceous Earth/Silica Based Toothpaste | |
| --- | --- |
| Poloxamer 338 | 2.00 |
| Deionized water | q.s. |

[1] a blend of 'Methocel K15M' and 'Methocel K100LV' in the ratio 1:5.
[2] 'Sident 9' available from Degussa.
[3] see Example 6.

EXAMPLE 6

| Flavour for use in the dentifrice of Example 5 | |
| --- | --- |
| Peppermint oil | 16.0% |
| Anethole | 20.0 |
| Menthol | 44.9 |
| L-Carvone | 10.7 |
| Methyl acetate | 1.6 |
| Eucalyptol | 5.3 |
| Limonene | 0.5 |
| Eugenol | 0.5 |
| Coriander Oil | 0.5 |

The flavour composition masked the bitter after-taste of chlorhexidine in the dentifrice and conferred a predominantly aniseed flavour to the dentifrice.

EXAMPLE 7

Process for the Preparation of the Dentifrice of Example 5

The dentifrice of Example 5 may be prepared by the following process:

1. Hydroxypropyl methylcellulose was slurried in glycerin (10% of the total volume).
2. Poloxamer 338 was dissolved in deionised water to give a 20% solution.
3. Sodium saccharin was dissolved in deionised water to give a 33% solution.
4. Thaumatin was dissolved in deionised water to give a 5% solution.
5. Deionized water (30% of total volume) was added to a heavy duty mixing vessel, followed by the hydroxpropyl methylcellulose slurry and the saccharin solution and this was then mixed for 5 minutes under vacuum.
6. Chlorhexidine gluconate solution was added and the mixture blended for a further 10 minutes under vacuum.
7. The remainder of the deionized water and glycerin were added, followed by mixing for a further 10 minutes under vacuum.
8. Silica and diatomaceous earth were sucked into the mixing vessel over 20 minutes with mixing, the mixture being mixed for a further 10 minutes, with vacuum being retained throughout.
9. The flavours and the thaumatin solution were then added, followed by mixing for a further 10 minutes under vacuum.
10. The poloxamer 338 solution was added, followed by mixing for a further 10 minutes under vacuum.
11. Sodium fluoride was added, followed by mixing for a further 15 minutes under vacuum.

BIOLOGICAL DATA

The data in the following table represents the potency of chlorhexidine in the dentifrice formulation, compared with a control containing chlorhexidine digluconate alone in aqueous solution and in the absence of the other agents listed. The assay is a standard agar diffusion method, using M. luteus as the assay organism.

| | Potency % |
| --- | --- |
| Example 1 | 79 |
| Example 2 | 59 |
| Example 3 | 90 |
| Example 4 | 90 |
| Control | 100 |

The data show that when chlorhexidine is incorporated into a dentifrice formulation according to the present invention, chlorhexidine substantially retains its potency, thereby allowing it to exert its intrinsic bacteriostatic activity within the oral cavity.

What is claimed is:

1. A dentifrice consisting essentially of:
   (a) 0.005 to 10% by weight of the dentifrice of chlorhexidine, or an orally acceptable acid addition salt thereof, in aqueous solution;
   (b) 0.01 to 30% by weight of the dentifrice of a nonionic thickening agent;
   (c) 0.005 to 20% by weight of dentifrice of a nonionic surfactant; and
   (d) 1 to 80% by weight of the dentifrice of a silica abrasive in which the anion content is less than 0.5%.

2. A dentifrice as claimed in claim 1 in which the nonionic thickening agent is a $(C_{1-6})$alkyl cellulose ether, or a $(C_{2-6})$ alkylene oxide modified $(C_{1-6})$alkylcellulose ether, or a mixture thereof.

3. A dentifrice as claimed in claim 2 in which the nonionic thickening agent is hydroxypropyl methylcellulose.

4. A dentifrice as claimed in claim 1 in which the nonionic surfactant is a polycondensate of ethylene oxide and propylene oxide.

5. A dentifrice as claimed in claim 4 in which the silica is a natural amorphous silica, or a synthetic amorphous silica, or a mixture thereof.

6. A dentifrice as claimed in claim 5 in which the natural amorphous silica comprises diatomaceous earth.

7. A dentifrice as claimed in claim 4 which comprises a fluoride salt.

8. A dentifrice as claimed in claim 7 in which the fluoride salt is incorporated to provide between 100 and 3000 ppm of fluoride.

9. A dentifrice as claimed in claim 7 in which the fluoride salt is an alkali metal fluoride.

10. A method for the prophylaxis or treatment of periodontal disease and/or caries, which method comprises the application of a dentifrice as defined in claim 1 to the oral cavity.

* * * * *